United States Patent [19]
Stordy

[11] Patent Number: 6,150,411
[45] Date of Patent: Nov. 21, 2000

[54] USE OF DHA AS A PHARMACEUTICAL COMPOSITION

[76] Inventor: Barbara Jacqueline Stordy, Weyvern House, Weyvern Park, Portsmouth Road, Peasmarsh, Guildford, Surrey, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,250

[22] PCT Filed: May 24, 1996

[86] PCT No.: PCT/GB96/01256

§ 371 Date: Feb. 28, 1997

§ 102(e) Date: Feb. 28, 1997

[87] PCT Pub. No.: WO96/37200

PCT Pub. Date: Nov. 28, 1996

[30] Foreign Application Priority Data

May 25, 1995 [GB] United Kingdom ........... 9510636

[51] Int. Cl.[7] ............ A61K 31/20; A61K 31/557
[52] U.S. Cl. ............ 514/559; 514/573; 514/912
[58] Field of Search ................. 514/559, 573, 514/912

[56] References Cited

PUBLICATIONS

Sakai et al, *Chemical Abstracts* 123:47841Y (Jul. 31, 1995).

Medline Abstract 96366943: Horrobin et al., 1995.

Biosis Abstract 97181672 (1994), Reme et al.

*Primary Examiner*—Zohreh Fay
*Attorney, Agent, or Firm*—Nixon & Vanderhye

[57] ABSTRACT

Dyslexia or inadequate night vision is treated by administering effective amounts of docosohexaenoic acid optionally in association wit other n-3 essential fatty acids and n-6 essential fatty acids.

12 Claims, 2 Drawing Sheets

USE OF DHA AS A PHARMACEUTICAL COMPOSITION

This is a 371 of PCT/GB96/01256 filed May 4, 1996 of the invention.

BACKGROUND

Dyslexia is a major problem of human development. It is a disorder manifest by difficulty in learning to read despite conventional instruction, adequate intelligence and socio-cultural opportunities, and arises from fundamental cognitive disabilities.

Dyslexia is four to five times commoner in boys than girls, commoner in children with atopic eczema and asthma than those without, and also commoner in offenders than the law abiding. It is associated with a loss of normal brain asymmetry which is demonstrable using modern brain scanning methods and also on functional tests. It is recognised to be a disorder with an organic basis.

Figure 1:
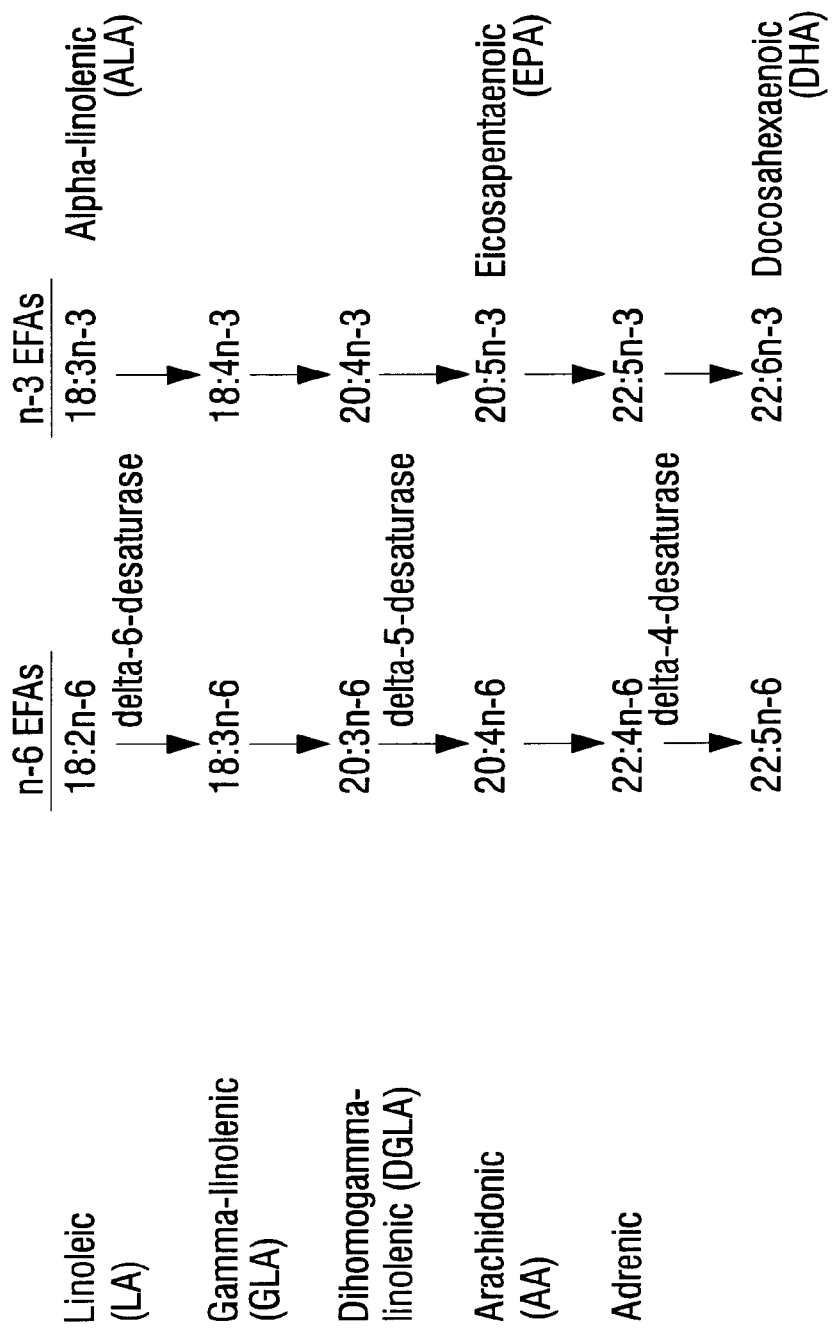
FIG. 1 is a flow chart showing the pathways of metabolism of LA and ALA.

Docosahexaenoic (DHA) is a major constituent of the retina, of nerve tissue and of the brain, and studies have now been done to look for abnormalities in dyslexic individuals in the intake of nutrients known to be important in brain function, particularly DHA. The first study looked at 33 dyslexic children and 48 controls and was directed to maternal diet during pregnancy. Mothers were given a comprehensive questionnaire, directed particularly at the levels of alpha-linolenic acid (ALA) in the diet and the ratio of ALA to linoleic acid (LA). (ALA is converted to DHA within the body and that conversion can be inhibited by a high intake of LA). The pathways of metabolism of LA and ALA are shown in FIG. 1. The study showed that the mothers of dyslexic children were significantly more likely to have consumed a diet with a low ALA:LA ratio during pregnancy.

A second study focused specifically on the intakes of foods, in particular fish and meats, which contain DHA itself. This study demonstrated that mothers of dyslexic children consumed diets lower in DHA.

It was therefore decided to investigate whether DHA supplementation might be beneficial in dyslexic individuals. A test capable of quickly demonstrating an effect was needed, and as DHA is known to be particularly important in the function of the retinal rods, required for vision in the dark, it was decided to test for reduced retinal DHA levels in dyslexia, as indicated by dark adaptation. Ten adults with dyslexia (4 females and 6 males) and ten control subjects (6 females and four males) were recruited. They were all young adults with age range of 18–26 years. Dark adaptation was tested using a standard instrument, the Friedman Visual Field Analyser, set for the dark adaptation function. One eye was occluded, bright light was shone in the other eye to bleach the retina and the room was darkened. Measurements of dark adaptation were made at one minute intervals by assessing the intensity of very brief flashes of light which could just be detected. Measurements were continued until no further adaptation was observed.

Because dark adaptation can be influenced by a number of known nutrients, including vitamins A and C, riboflavin, nicotinic acid, thiamin and zinc, all subjects were asked to keep a careful 7 day record of food eaten and the results analysed by the diet analysis program, COMPEAT 4. No differences between the control and dyslexia groups in any of these nutrients were detected.

Figure 2:
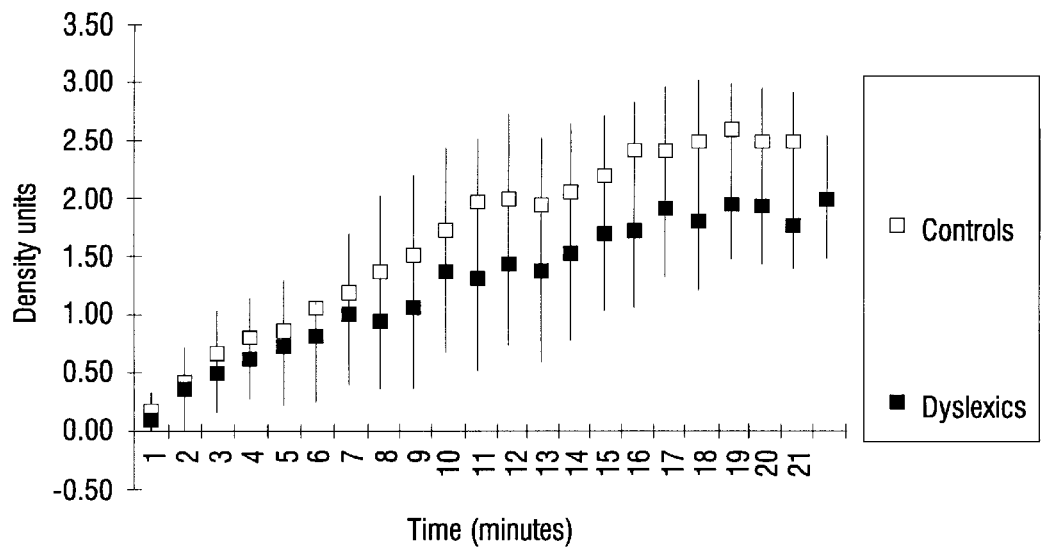
FIG. 2 is a graph showing dark adaptation in dyslexics compared with non-dyslexic controls.

The results for the two groups are presented in FIG. 2 which shows the means and standard deviations. The dyslexics at every time point show poorer dark adaptation than the controls and the differences between the two groups are statistically significant $p<0.05$).

Tests for influence of DHA on dark adaptation was therefore conducted. For a period of one month 5 dyslexics and 5 controls were given 4 capsules per day of a fish oil which contained 120 mg of DHA per capsule, with no vitamin A or vitamin D. Dark adaptation was then retested.

Figure 3:
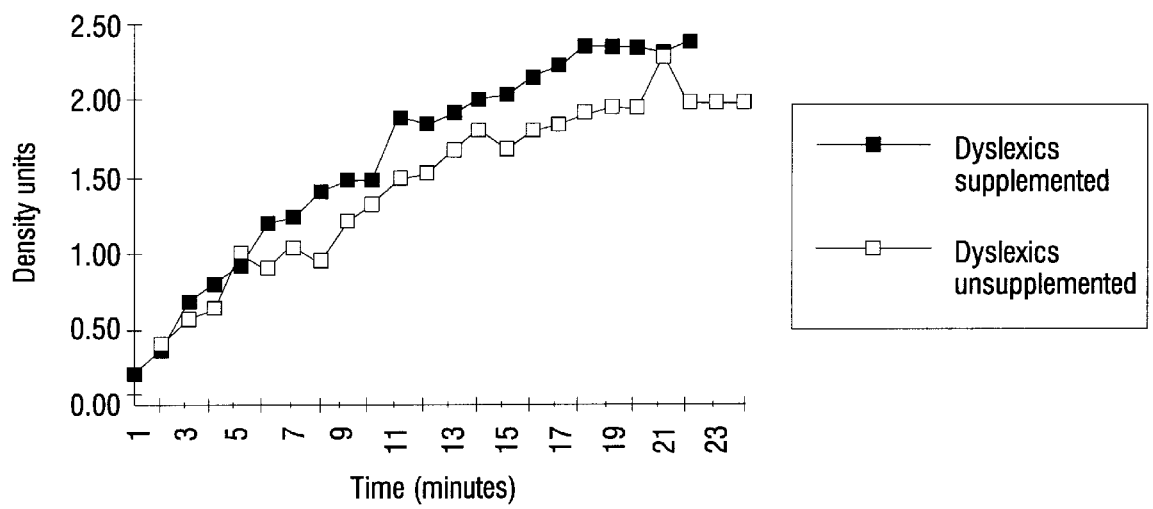
FIG. 3 is a graph showing the effect of fish oil supplementation on dark adaption in dyslexics.

In four of the controls, DHA had no effects on dark adaptation, although in one subject adaptation clearly improved. In contrast, in the dyslexic subjects as shown in FIG. 3, DHA consistently and significantly improved dark adaptation ($p < 0.041$).

Subsequently, DHA supplements given to dyslexic children have been found to be associated with apparent improvements in reading ability and behaviour. These reports are currently anecdotal and subjective but more formal controlled studies are in preparation.

DESCRIPTION OF THE INVENTION

The invention lies in combating dyslexia or inadequate night vision or dark adaptation in dyslexics or normal individuals, by administering DHA or a precursor n-3 EFA, and particularly in:

1. A method of treating the conditions by administering DHA or precursor to children and adults showing them.

2. A method of preventing the conditions by administering DHA or precursor to women during pregnancy and to infants in the year after birth.

The invention also lies in a method of preparation of a medicament, for use in combating dyslexia or inadequate night vision or dark adaptation as above, when DHA or precursor is used.

Although DHA is a key fatty acid in both the retina and the brain, the n-6 fatty acids derived from linoleic acid (FIG. 1) are also important in these tissues. Because DHA and eicosapentaenoic acid (EPA) (which is usually associated with DHA in fish oils) can in some circumstances inhibit conversion of LA to gamma-linolenic acid (GLA), it may be appropriate in some situations to provide, with the DHA, supplements of LA or preferably GLA, dihomo-gamma-linolenic acid (DGLA) or arachidonic acid (AA) to prevent depletion of these important fatty acids. It may also be appropriate to provide other n-3 essential fatty acids such as alpha-linolenic acid, stearidonic acid (SA) or EPA for their specific properties rather than as DHA precursors.

The fatty acids may be delivered in any appropriate form which can raise the levels of DHA and/or the other fatty acids in the blood. Appropriate forms are the free fatty acids; their salts. including lithium salts: esters; diesters of 1,3-propane diol and other diols; amides; alcohols; tri-, di- and monoglycerides; phospholipids such as phosphatidyl-choline or phosphatidyl-ethanolamine; or any other pharmaceutically acceptable combined form.

The fatty acids are not toxic and so they may be given in doses of from 1 mg to 100 g per day, preferably 20 mg to 10 g and very preferably 50 mg to 2 g/day. They may be administered orally, enterally, parenterally or topically by any appropriate formulation including capsules, pastilles, tablets, powders, emulsions, suspensions, oils, creams, lotions, patches, liposomes, galactosomes or any other form known to those skilled in the art.

The use of DHA as such is preferred. The ratio of DHA to n-6 acids, when present, in the formulations may range from 1:100 to 100:1, preferably 5:1 to 1:5 and very preferably 3:1 to 1:3.

EXAMPLES

The following formulations and their use illustrate the invention, by way of example.

1. For use in combating dyslexia, soft gelatin capsules or hard gelatin capsules, or pastilles or tablets or other pharmaceutical or nutritional dosage forms containing 100 mg DHA and optionally 100 mg GLA, 100 mg AA and/or 100 mg EPA, for pre-emptive consumption by women in pregnancy or by infants, or for consumption by diagnosed dyslexic children or adults, to give a daily dose of DHA of 20 mg to 10 g.

2. Granules or powder for use as above, made with gum acacia, gelatin, starch or other appropriate material containing by weight in each gram, 50 mg DHA, optionally with 50 mg of DGLA, 50 mg AA and/or 50 mg SA.

3. Oils for use as above for use as salad oils or for incorporation into any appropriate food material containing 5% by weight DHA, optionally with 10% by weight GLA, 5% by weight AA and 5% by weight EPA.

4. Whips, foams, creams, mousses or other liquid or semi-liquid formulations for use as above as foods and containing 2% DHA and optionally 2% by weight GLA, 2% AA, 2% DGLA, 2% SA and 2% EPA.

5. Creams, ointments, lotions, shampoos, patches, sticks, pessaries, suppositories or any other dosage form for use as above for topical application in which the active material is an oil containing 3% DHA, optionally with 5% by weight DGLA, 2% AA and 3% EPA.

6–10. Formulations as in 1–5 but in which the active ingredients are DHA with any one (or more than one) of the n-6 EFAs selected from GLA, DGLA and AA, and/or any one (or more than one) of the n-3 EFAs selected from SA, 20:4 n-3, DPA or EPA.

11–15. Formulations as in 1–5 but in which the active ingredients are DHA and either GLA or DGLA of the n-6 series and/or EPA of the n-3 series.

16–20. Formulations as in 1–5 but for use in improvement of dark adaptation and/or nocturnal vision generally in dyslexic or non-dyslexic individuals.

What is claimed is:

1. A method of treating dyslexia comprising administering to a subject in need of same docosahexaenoic (DHA) in an effective amount.

2. A method according to claim 1, administration being to children or adults showing one or more of the conditions.

3. A preventative method according to claim 1, administration being to women during pregnancy or to infants in the year after birth.

4. A method according to claim 1 wherein one or more n-6 essential fatty acids (EFAs) selected from the group consisting of linoleic, gamma-linolenic, dihomogamma-linolenic and arachidonic acids and/or one or more n-3 EFAs selected from the group consisting of alpha-linolenic, stearidonic and eicosapentaenoic acids is used in addition to the DHA.

5. A method according to claim 1, wherein a precursor n-3 essential fatty acid is substituted for all or part of the DHA.

6. A method according to claim 2, 3 or 1 wherein administration is 1 mg to 100 g per day of the DHA.

7. A method according to claim 4 wherein administration is of DHA and n-6 essential fatty acids in a weight ratio of 1:100 to 100:1.

8. A method according to claim 1 wherein the DHA and/or other essential fatty acids are present as one or more of: salts including lithium salts; esters; diesters of 1,3-propane diol and other diols; amides; fatty acid alcohols; mono-, di- or triglycerides; phosphatidyl-choline, phosphatidyl-ethanolarnine or other phospholipid; or other pharmaceutically acceptable combined form.

9. A method according to claim 6 wherein 20 mg to 10 g of DHA is administered.

10. A method according to claim 9 wherein 50 mg to 2 g of DHA is administered.

11. A method according to claim 7 wherein the weight ratio is 5:1 to 1:5.

12. A method according to claim 11 wherein the weight ratio is 3:1 to 1:3.

* * * * *